United States Patent
Ankorina-Stark et al.

(10) Patent No.: US 11,969,523 B2
(45) Date of Patent: Apr. 30, 2024

(54) STEM CELL COMPOSITION

(71) Applicant: Contura International A/S, Søborg (DK)

(72) Inventors: Ieva Ankorina-Stark, Nivå (DK); Lise Hanne Christensen, Frederiksberg (DK); Miguel A. Valdés Vázquez, Manilva (ES)

(73) Assignee: Contura International A/S, Søborg (DK)

( * ) Notice: Subject to any disclaimer, the term of this patent is extended or adjusted under 35 U.S.C. 154(b) by 508 days.

(21) Appl. No.: 16/607,304

(22) PCT Filed: Apr. 24, 2018

(86) PCT No.: PCT/DK2018/050078
§ 371 (c)(1),
(2) Date: Oct. 22, 2019

(87) PCT Pub. No.: WO2018/196934
PCT Pub. Date: Nov. 1, 2018

(65) Prior Publication Data
US 2020/0376166 A1    Dec. 3, 2020

(30) Foreign Application Priority Data

Apr. 24, 2017 (EP) .................................. 17167690

(51) Int. Cl.
*A61L 27/52* (2006.01)
*A61L 27/16* (2006.01)
*A61L 27/38* (2006.01)
*C08L 33/26* (2006.01)

(52) U.S. Cl.
CPC ........... *A61L 27/3834* (2013.01); *A61L 27/16* (2013.01); *A61L 27/386* (2013.01); *A61L 27/52* (2013.01); *C08L 33/26* (2013.01); *A61L 2400/06* (2013.01); *A61L 2430/10* (2013.01)

(58) Field of Classification Search
CPC ...... A61L 27/3834; A61L 27/16; A61L 27/52; A61L 27/386; A61L 2400/06; A61L 2430/10; C08L 33/26
See application file for complete search history.

(56) References Cited

U.S. PATENT DOCUMENTS

2002/0064512 A1  5/2002  Petersen et al.
2014/0072601 A1*  3/2014  Connon

FOREIGN PATENT DOCUMENTS

| WO | 02/16453 A1 * | 2/2002 |
| WO | WO 2006/014159 A2 | 2/2006 |
| WO | WO 2012/123385 A1 | 9/2012 |
| WO | WO 2013/086523 A2 | 6/2013 |
| WO | WO 2013/174982 A1 | 11/2013 |
| WO | WO 2015/186906 A1 | 12/2015 |
| WO | 2016/004068 A1 * | 1/2016 |

OTHER PUBLICATIONS

Engler (Cell, 126, pp. 677-689, Aug. 25, 2006) (Year: 2006).*
Database WPI—XP002774108—Dec. 10, 2015.
International Search Report for PCT/DK2018/050078 dated Jul. 18, 2018.
Smith, R.K.W. et al., "Isolation and implantation of autologous equine mesenchymal stem cells from bone marrow into the superficial digital flexor tendon as a potential novel treatment" Equine Veterinary Journal, 2003, pp. 99-102, vol. 35, No. 1.
Narins, Rhoda S. et al., "Polyacrylamide hydrogel differences: getting rid of the confusion" Journal of Drugs in Dermatology, Dec. 2011, pp. 1370-1375, vol. 10, No. 12.

* cited by examiner

*Primary Examiner* — Alma Pipic
(74) *Attorney, Agent, or Firm* — Knobbe Martens Olson & Bear LLP (57) ABSTRACT

The present invention relates to a composition comprising stem cells, a cell culture medium and a polyacrylamide hydrogel (PAAG), wherein the PAAG contains less than 0.02% $W_{monomer}/W_{total\ PAAG}$] of a N-hydroxyethyl acrylamide (HEA) side chain. The invention also relates to the process of making the composition. In particular, the present invention relates to the composition, wherein the composition is administered by injection and wherein it is used in medicine, in particular for use in prevention and/or treatment of e.g. tendon injury in a mammal, arthritis in a mammal or arthropathy in a mammal. Tendon injury, arthritis or arthropathy may occur in a human, a racing animal or a companion animal.

15 Claims, 5 Drawing Sheets

STEM CELL COMPOSITION

CROSS REFERENCE TO RELATED APPLICATIONS

This application is a U.S. National Phase Application of PCT International Application Number PCT/DK2018/050078, filed on Apr. 24, 2018, designating the United States of America and published in the English language, which is an International Application of and claims the benefit of priority to European Patent Application No. 17167690.1, filed on Apr. 24, 2017. The disclosures of the above-referenced applications are hereby expressly incorporated by reference in their entireties.

TECHNICAL FIELD OF THE INVENTION

The present invention relates to a composition comprising stem cells, a cell culture medium and a polyacrylamide hydrogel (PAAG), wherein the PAAG contains less than 0.02% $w_{monomer}/w_{total\ PAAG}$] of a N-hydroxyethyl acrylamide (HEA) side chain.

In particular the present invention relates to the composition, wherein the composition is administered by injection and wherein it used in medicine, in particular for use in prevention and/or treatment of tendon injury in a mammal, arthritis in a mammal or arthropathy in a mammal.

BACKGROUND OF THE INVENTION

A tendon in a mammal is a tough band of firm fibrous connective tissue that usually connects muscle to bone thus withstanding tension. A ligament is similar to tendon but connects bone to bone. Ligaments are found e.g. in joints. Ligaments mainly stabilize movements whereas tendons control movements.

Ligaments as well as tendons are firmly connected longitudinally oriented strands of connective tissue that is aligned in parallel orientation along their longitudinal axis. However, upon wear and tear these strands may break, either partly or completely, and healing following surgery is prolonged due to the poor inherent healing capacity of the tissue. Also, there is a paucity of blood vessels within this type of tissue.

With age, overuse and/or lack of use, ligaments and tendons may degenerate, causing the longitudinal strands to be disorientated and later calcified, increasing the risk of rupture.

Currently, the only method available for repairing torn ligaments or tendons is surgical intervention, typically a tissue graft using the patient's own tissue from a different part of the body. This is a lengthy procedure, which is invasive and may not restore the full use of the torn or damaged ligaments or tendons. Typical recovery times before the tendon or ligament in question is stable range from 0.5 to 1 years.

There is therefore a need in the art for an alternative or improved method of repairing torn or damaged ligaments or tendons, which is less invasive than existing methods, which improves the use or restores the full use of the tendon or ligament, and which results in a faster recuperation.

Arthropathy in a mammal is a general term for joint pain and/or instability, of which arthritis caused by inflammation of the synovial membrane and destruction of the cartilage is the most common. The disease is wide-spread, and long-lasting effective non-surgical treatment is lacking.

There is therefore a need in the art for an alternative or improved method of treating and/or preventing arthropathy, which results in less joint pain and/or less instability of the joint.

Arthritis is a group of conditions involving damage to the joints of the body i.e. pain caused by inflammation and cartilage destruction. There are over 100 different forms of arthritis.

There is a need in the art for an alternative or improved method of treating and/or preventing arthritis, which results in less inflammation and cartilage destruction.

Most human tissues do not regenerate spontaneously; this is why cell therapies and tissue engineering are promising alternatives. The principle is simple: cells are collected from a patient and introduced directly into the damaged tissue or via a three-dimentional porous support and then harvested in a bioreactor in which the physico-chemical and mechanical parameters are controlled. Once the tissues (or the cells) are mature they may be implanted.

Recent work in the field has demonstrated that mesenchymal stem cells (MSCs) derived from bone marrow improves the healing of tendon injuries in the horse.

MSCs are injected in large numbers (10-20 million cells) but only <25% remain in the injury area after 24 hours.

Thus, there is a need in the art for a suitable delivery system for the stem cell delivery, and this delivery system need to be safe and non-toxic to the patient. Various hydrogels exist in the art, e.g. "Notrex, "Amazingel", Aqualift etc. However, major differences in the chemical composition, physical properties, manufacturing, and injection techniques exist between these hydrogels, making them quite different. Polyacrylamide hydrogels are considered to be the same products, but this is not the case. This is discussed in a paper by Narins R. S. and Schmidt R., "Polyacrylamide Hydrogel Differences: Getting rid of the confusion", Journal of Drugs in Dermatology, Vol 10, Issue 12, December 2011, p. 1370. The safety of polyacrylamide hydrogels is determined based on a combination of the chemical and physical properties, the stability and reliability of the product as well as the implantation technique.

Another work in the field (WO 2013/086523) has investigated the suitability of a hydrogel, which may be suitable for bone regeneration, in cell culture studied comprising rat fibroblasts for cytocompatibility of hydrogel leachables formed by polymerising of the hydrogel. The gel is formed from a poly(N-isopropylacrylamide)-based macromere and a polyamidoamine-based macromere. Hence, the gel is a thermoresponsive poly-NiPAAm-gel and not a crosslinked polyacrylamide gel as disclosed in the present invention. The poly-NiPAAm-gel solidifies upon injection into the body, forming a multi-cross-linked gel, thereby releasing potential toxic leachable products in situ. Further, the gel is degradable within 12 weeks, which further releases toxic products to the body.

Hence, an improved stem cell delivery system that solves the above problems of stability of the gel and that does not release toxic components in situ would be advantageous, and in particular a more efficient and/or reliable stem cell scaffold delivery system that would secure stable growth of stem cells would be advantageous.

Also, an improved stem cell delivery system that solves the above problems of degradability of the gel would be advantageous, and in particular a more stable stem cell scaffold delivery system would be advantageous.

Hence, an improved stem cell delivery system would be advantageous, and in particular a more efficient and/or reliable stem cell scaffold delivery system would be advantageous.

Also, an alternative or improved stem cell delivery system would be advantageous for use in medicine, in particular for use in prevention and/or treatment of tendon injury in a mammal, arthritis in a mammal or arthropathy in a mammal.

Surprisingly, the inventors have found that a composition comprising stem cells, a cell culture medium and PAAG, wherein the PAAG contains less than 0.02% $w_{monomer}/w_{total\ PAAG}]$ of a N-hydroxyethyl acrylamide (HEA) side chain or no HEA side chain, is useful as a scaffold delivery system. In fact, it was surprisingly found that stem cells such as equine mesenchymal stem cells embedded in this scaffold remain viable, proliferate and migrate when PAAG is used as a scaffold in equine tendon tissue, and the composition does not induce a pro-inflammatory response. Accordingly, the present invention surprisingly demonstrated that the composition comprising stem cells, a cell culture medium and PAAG may be used as a scaffold in the repair of tendinopathy.

Without being bound by theory, it is hypothesised that physical retention of cells will encourage these cells to engraft into the tissue with the result of increased numbers that contribute to tissue healing and further improve their beneficial effects.

Surprisingly, the present inventors have found that a composition comprising stem cells, a cell culture medium and PAAG presents a solution to the problem of delivery of stem cells within a pliable, injectable and biocompatible gel that is tolerated clinically and compatible with stem cell survival and growth.

SUMMARY OF THE INVENTION

Thus, an object of the present invention relates to providing a composition comprising stem cells, a cell culture medium and a polyacrylamide hydrogel (PAAG), wherein the PAAG contains less than 0.02% $w_{monomer}/w_{total\ PAAG}]$ of a N-hydroxyethyl acrylamide (HEA) side chain.

In particular, it is an object of the present invention to provide a composition that solves the above mentioned problems of the prior art with stem cell delivery system not being efficient and/or being an unreliable stem cell scaffold delivery system.

Thus, one aspect of the invention relates to a composition comprising stem cells, a cell culture medium and a polyacrylamide hydrogel (PAAG), wherein the PAAG contains less than 0.02% $w_{monomer}/w_{total\ PAAG}]$ of a N-hydroxyethyl acrylamide (HEA) side chain.

Another aspect of the present invention relates to the composition according to the invention, wherein the composition is administered by injection.

Yet another aspect of the present invention is to provide a process for making the composition according to the invention, comprising the steps of: i) providing stem cells, a cell culture medium and a polyacrylamide hydrogel (PAAG), wherein the PAAG contains less than 0.02% $w_{monomer}/w_{total\ PAAG}]$ of a N-hydroxyethyl acrylamide (HEA) side chain, ii) mixing the components of i) thereby achieving the composition.

Still another aspect of the present invention is to provide a composition obtainable by the process of the invention.

Still a further aspect of the present invention is to provide a composition according to the invention, for use in medicine.

Still yet a further aspect of the present invention is to provide a composition according to the invention, for use in prevention and/or treatment of tendon injury in a mammal.

In one embodiment, the invention relates to a method for the prevention and/or treatment of tendon injury in a mammal, the method comprising administering to said mammal a composition according to the invention.

In another embodiment, the invention relates to use of a composition of the invention for preparation of a medicament for prevention and/or treatment of tendon injury in a mammal.

Still another aspect of the present invention is to provide a composition according to the invention, for use in prevention and/or treatment of arthritis in a mammal.

In a further embodiment, the invention relates to a method for the prevention and/or treatment of arthritis in a mammal, the method comprising administering to said mammal a composition according to the invention.

In yet another embodiment, the invention relates to use of a composition of the invention for preparation of a medicament for prevention and/or treatment of arthritis in a mammal.

Yet another aspect of the present invention is to provide a composition according to the invention, for use in prevention and/or treatment of arthropathy in a mammal.

In still one embodiment, the invention relates to a method for the prevention and/or treatment of arthropathy in a mammal, the method comprising administering to said mammal a composition according to the invention.

In still another embodiment, the invention relates to use of a composition of the invention for preparation of a medicament for prevention and/or treatment of arthropathy in a mammal.

Still yet a further aspect of the present invention is to provide a composition according to the invention, for use in prevention and/or treatment of urinary incontinence in a mammal.

In still one embodiment, the invention relates to a method for the prevention and/or treatment of urinary incontinence in a mammal, the method comprising administering to said mammal a composition according to the invention.

In still another embodiment, the invention relates to use of a composition of the invention for preparation of a medicament for prevention and/or treatment of urinary incontinence in a mammal.

Still yet a further aspect of the present invention is to provide a composition according to the invention, for use in prevention and/or treatment of anal incontinence in a mammal.

In still one embodiment, the invention relates to a method for the prevention and/or treatment of anal incontinence in a mammal, the method comprising administering to said mammal a composition according to the invention.

In still another embodiment, the invention relates to use of a composition of the invention for preparation of a medicament for prevention and/or treatment of anal incontinence in a mammal.

Still yet a further aspect of the present invention is to provide a composition according to the invention, for use in prevention and/or treatment of functional or cosmetic defects of the face or body in a mammal.

In still one embodiment, the invention relates to a method for the prevention and/or treatment of functional or cosmetic defects of the face or body in a mammal, the method comprising administering to said mammal a composition according to the invention.

In still another embodiment, the invention relates to use of a composition of the invention for preparation of a medicament for prevention and/or treatment of functional or cosmetic defects of the face or body in a mammal.

BRIEF DESCRIPTION OF THE FIGURES

FIG. 3a shows proliferation assay data readouts of MSCs encapsulated in PAAG. The percentage of cells alive was quantified using a cell vitality dye (live-dead assay) at the time points indicated. The number of live cells and dead cells counted within a standardized field of view under the microscope are shown as indicated in the appropriate column.

FIG. 3b shows the migration ability of PAAG encapsulated-MSCs onto tendon matrix. A) Nonviable Native Tendon Matrices (NNTs) were prepared by cutting small sections, which were devoid of all endogenous cells. These were placed within a well of a tissue culture plate with two PAAG beads (clear gels) containing MSCs labeled with green fluorescent dye on top of each section and co-cultured for 5 days.

B) Viable fluorescent-labelled cells (arrows marking green signal) have adhered to the matrix of the tendon at 5 days. (×200)

C) Viable cells are seen together with weakly stained dead cells (arrows), most of these being resident tenocytes lying in aligned rows. (×200)

FIG. 4a shows the external aspect of a limb with the deep digital flexor tendon 14 days post injection. A: view of the entire distal limb. B: detail over the injection sites. The swelling is noticeable on both the palmar and lateral aspects (white arrows).

FIG. 4b shows an ultrasonographic image of case 4a.

A) image taken immediately after the intratendinous injection. The air from the injection is visible (arrow). B: the area 24 h post injection. The air has disappeared but the swelling remains.

The present invention will now be described in more detail in the following.

DESCRIPTION OF THE INVENTION

Definitions

Prior to discussing the present invention in further details, the following terms and conventions will first be defined:

The PAAG is prepared as described in WO 02/16453, and further in WO 2012/123385 hereby incorporated by reference. The PAAG may comprise any embodiment of the hydrogel as described in WO 02/16453 and WO 2012/123385. The PAAG is further described below in the section Preparation of the polyacrylamide hydrogel (PAAG).

The term stem cell used herein refers to undifferentiated or immature biological cells that can differentiate into specialized cells and can divide through mitosis. In mammals, there are two broad types of stem cells: embryonic (or genuine) stem cells, which are isolated from the inner cell mass of blastocysts, and adult stem cells (progenitor type stem cells or induced pluripotent stem cells (iPS cells), which are found in various tissues. In adult organisms, all three types of stem cells can act as repair agents for the body, replenishing specialized tissues.

A progenitor type stem cell is a biological cell that has a tendency to differentiate into a specific type of cell. It is already more specialized than an embryonic stem cell and can just be further pushed to differentiate into its "target" cell. Induced pluripotent stem cells (iPS cells) are adult cells, which have been reversed into the embryonic state by using 4 embryonic transcription factors. The most important difference between embryonic (or induced embryonic) stem cells and progenitor cells is the fact that the former cell types are not tissue specific and can replicate indefinitely, whereas progenitor type cells are tissue specific and can divide only a limited number of times.

Types of stem cells according to this invention include progenitor type stem cells, embryonic stem cells and iPS cells. According to the invention, stem cells are preferred, and more preferred are progenitor type stem cells. Progenitor type stem cells include stem cells from all sorts of mammalian tissue such as e.g. from muscle, bone, blood, nervous system or skin.

A certain type of progenitor type stem cells are mesenchymal stem cells (MSCs)—or stromal cells—which are multipotent stromal cells that can differentiate into a variety of lineages, including osteocytes, adipocytes and chondrocytes. According to the invention, MSCs are even further preferred.

Arthramid® gel is a commercial PAAG product defined with the following physical and chemical characteristics: Dry matter content is 2.5% polyacrylamide, elasticity modulus is 33-55 Pa, the pH is 7.3-8.2 and the amount of the remaining monomers acrylamide and cross-linking agent is below 1.5 ppm).

The physio and chemical product characteristics of the PAAG are very important for the ability of stem cells to survive and divide with success in the gel i.e. the dry matter content, elasticity modulus, pH etc., all determine the stability of the gel and thus affect the ability of the stem cells to survive and divide. Also, the physio and chemical product characteristics of the PAAG are important for the tissue interaction and lack of degradability of the PAAG upon injection into a tissue, also when the PAAG is loaded with stem cells.

DETAILED DESCRIPTION OF THE INVENTION

In one aspect, the invention relates to a composition comprising stem cells, a cell culture medium and a polyacrylamide hydrogel (PAAG), wherein the PAAG contains less than 0.02% $w_{monomer}/w_{total\ PAAG}$] of a N-hydroxyethyl acrylamide (HEA) side chain.

In an embodiment, the invention relates to a composition consisting essentially of stem cells, a cell culture medium and a polyacrylamide hydrogel (PAAG), wherein the PAAG contains less than 0.02% $w_{monomer}/w_{total\ PAAG}$] of a N-hydroxyethyl acrylamide (HEA) side chain.

In an embodiment, the invention relates to a composition consisting of stem cells, a cell culture medium and a polyacrylamide hydrogel (PAAG), wherein the PAAG contains less than 0.02% $w_{monomer}/w_{total\ PAAG}]$ of a N-hydroxyethyl acrylamide (HEA) side chain.

The inventors have surprisingly found that a composition of the invention is highly suitable as a scaffold for delivery of stem cells, preferably such as mesenchymal stem cells (MSCs) in the horse. The PAAG preserves the viability, proliferation for days and migration of the stem cells, preferably such as of MSCs, and the cells engraftment into the tendon matrix. Also, there is no inflammatory response modulated by interleukin 1 beta (IL-1β). In fact, the data surprisingly demonstrated that an uninhibited ability of the cells to divide in PAAG for at least 5 days. IL-1β is a cytokine known by the person skilled in the art as a marker of inflammatory responses i.e. this cytokine is an important mediator of the inflammatory response, and is involved in a variety of cellular activities, including cell proliferation, differentiation, and apoptosis.

Further, the use of PAAG is safe when administered in normal equine tendons since no infections, adverse reactions or lameness are associated with the treatment. Also, the use of PAAG as a scaffold for stem cells, preferably such as MSCs in the horse joint, allows a more even distribution of the cells within the joint.

This finding is surprising, as others have not been able to show viability, proliferation and migration of a composition comprising stem cells, a cell culture medium and a PAAG, wherein the PAAG contains less than 0.02% $w_{monomer}/w_{total\ PAAG}]$ of a N-hydroxyethyl acrylamide (HEA) side chain. For instance, in e.g. WO 2013/174982, it is shown that a polyacrylamide gel did neither adsorb nor retain extracellular (ECM) peptides.

Surprisingly, it has been shown that the combination of low dry matter content together with specific elasticity modulus and low residual monomer concentration of the PAAG of the present invention that gives the unique effects of stem cell survival in the gel.

In one embodiment, the invention relates to a composition wherein the PAAG contains less than 0.02% $w_{monomer}/w_{total\ PAAG}]$ of a N-hydroxyethyl acrylamide (HEA) side chain, such as less than 0.015%, such as less than 0.010%, such as less than 0.005%. By using a washing process, residual monomers may be removed and/or reduced in amount. Typically, the washing process is to be done in such a manner and for such as duration so as to lower the residual monomeric content to no more than 50 ppm, preferably no more than 40 ppm, such as no more than 30 ppm, more preferably no more than 20 ppm, even more preferably no more than 10 ppm, most preferably no more than 5 ppm, such as no more than 4 or 3 or even more preferred no more than 1.5 ppm. Regulatory standards for acceptable levels of residual monomeric content in order for the gel to be considered biocompatible may vary but are often set at no more than 10 ppm, more often no more than 5 ppm.

The HEA side chain has the chemical formula as seen below:

In one embodiment, the invention relates to a composition wherein the PAAG does not contain a HEA side chain. In other words, neither monomers nor polymers in the PAAG contain HEA side chains. This means that the PAAG contains 0.00% HEA side chain, or only trace amounts of HEA such as no more than 1.5 or no more than 1 ppm.

In an embodiment, the invention relates to a composition consisting essentially of stem cells, a cell culture medium and a polyacrylamide hydrogel (PAAG), wherein the PAAG does not contain a HEA side chain.

In a further embodiment, the invention relates to a composition consisting of stem cells, a cell culture medium and a polyacrylamide hydrogel (PAAG), wherein the PAAG does not contain a HEA side chain.

In a further embodiment, according to the invention, the side chain may also be wherein X is a $C_1$-$C_6$ alkyl further comprising a function selected from the group consisting of hydroxyl, carboxy, amine and aldehyde. According to the invention, the PAAG preferably does not contain such a side chain, i.e. the PAAG does not contain the side chain wherein X is a $C_1$-$C_6$ alkyl further comprising a function selected from the group consisting of hydroxyl, carboxy, amine and aldehyde. When X=—$C_2H_4OH$, then the side chain is HEA.

According to the invention, the PAAG contains less than 0.02% $w_{monomer}/w_{total\ PAAG}]$ of a N-hydroxyethyl acrylamide (HEA) side chain.

According to the invention, this means that the weight percent of the monomers that have HEA side chains is less than 0.02% of the total weight of the resulting PAAG. The resulting PAAG consists of a mixture of monomers and polymers. Hence, only the monomers present in the final PAAG may have very small amounts of HEA side chains (less than 0.02% of the total weight of the PAAG). In a preferred embodiment, the monomers do not contain HEA side chains. In another even more preferred embodiment, the final PAAG does not contain HEA side chains. All percentages are in weight ratios; i.e. weight monomer:total PAAG weight.

The a cell culture medium according to the invention may be any conventional and suitable cell culture medium for the cells at hand, such as e.g. BME, MEM, DMEM, RPMI, McCoys 5A Hams F-12. Cell culture conditions can vary for each cell type, but artificial environments consist of a suitable vessel with substrate or medium that supplies the essential nutrients (amino acids, carbohydrates, vitamins, minerals), growth factors, hormones, and gases ($CO_2$, $O_2$), and regulates the physio-chemical environment (pH buffer, osmotic pressure, temperature). Most cells require a surface or an artificial substrate (adherent or monolayer culture)

whereas others can be grown free floating in culture medium (suspension culture). The preferred cell culture medium is suitable for growth and proliferation of stem cells. The most preferred cell culture medium according to the invention is D10 medium (Dulbecco's Modified Eagle Medium, DMEM, supplemented with fetal bovine serum (10% v/v), 100 U/ml penicillin, and 100 U/ml streptomycin).

In one embodiment, the invention relates to a composition wherein the stem cells are selected from at least one of embryonic (or genuine) stem cells or adult stem cells.

In one embodiment, the invention relates to a composition wherein the stem cells are selected from at least one of progenitor type stem cells, embryonic stem cells or induced pluripotent stem cells, such as from at least two of progenitor type stem cells, embryonic stem cells or induced pluripotent stem cells.

In yet a preferred embodiment, the invention relates to a composition wherein the stem cells are selected from at least one of progenitor type stem cells, or induced pluripotent stem cells.

In one embodiment, the invention relates to a composition wherein the stem cells are mesenchymal stem cells. The mesenchymal stem cells are particularly preferred, and even more preferred are bone marrow mesenchymal stem cells.

In one embodiment, the invention relates to a composition wherein the composition is administered by injection.

The injection of the composition of the invention may be performed under local anaesthesia, but local anaesthesia is not necessarily required. However, the procedure is preferably performed under sterile conditions. Any hair covering the injection area is cropped and the skin thoroughly rinsed e.g. with chlorhexidine and ethanol (e.g. 3 times interchangeably). Then, the cannula is inserted into the joint cavity and it is checked by aspiration that it is placed properly intraarticularly. Generally, the joint is emptied for at least the amount of liquid which it has been decided to inject and the desired amount of the PAAG is then injected. An antibiotic may be included in the PAAG in order to prevent iatrogenic infection of the joint. According to an embodiment of the invention, the composition is administered by intraarticular injection and/or by tendon injection and/or by ligament injection. According to the invention, the injection is preferably in a mammal.

A tendon in a mammal is a tough band of firm fibrous connective tissue that usually connects muscle to bone thus withstanding tension. A ligament is similar to tendon but connects bone to bone.

The healing process for a broken tendon or ligament may be long and painful, but healing and recovering occurs in a process that is controlled by the cells and their surrounding extracellular matrix, a process that is surprisingly shortened and strengthened by the application of stem cells in PAAG.

It has surprisingly been found that the composition of the invention may be used as improving the joint instability and/or for providing a pain alleviating effect.

Arthropathy in a mammal is a general term for joint pain and/or instability, of which arthritis caused by inflammation of the synovial membrane and destruction of the cartilage is the most common. The disease is wide-spread, and long-lasting effective non-surgical treatment is lacking. PAAG injected into the joint cavity has shown to alleviate the pain associated with arthritis, possibly through a cushioning effect.

In one embodiment, the invention relates to the composition, wherein 0.1-50 ml composition is administered by injection once, such as twice, such as three times, such as four times, such as 5 times, such as 6 times, such as 7 times, such as 8 times, such as 9 times, such as 10 times.

In one embodiment, the invention relates to a composition wherein the intraarticular cavity and/or the central core of the flexor tendon and/or the suspensory ligament is injected.

In one embodiment, the invention relates to a composition wherein 0.1-50 ml composition is administered by injection once every 2 weeks, such as every 4 weeks, such as every 6 weeks, such as every 8 weeks, such as every 10 weeks, such as every 12 weeks, such as every 14 weeks, such as every 16 weeks or such as even longer.

In one embodiment, the invention relates to a composition wherein the intraarticular cavity and/or the central core of the flexor tendon and/or the suspensory ligament is injected.

In an aspect, the invention relates to a process for making the composition, comprising the steps of: i) providing stem cells, a cell culture medium and a polyacrylamide hydrogel (PAAG), wherein the PAAG contains less than 0.02% $w_{monomer}/w_{total\ PAAG}$] of a N-hydroxyethyl acrylamide (HEA) side chain, ii) mixing the components of i) thereby achieving the composition.

In an embodiment, the invention relates to a process for making the composition, consisting essentially of the steps of: i) providing stem cells, a cell culture medium and a polyacrylamide hydrogel (PAAG), wherein the PAAG contains less than 0.02% $w_{monomer}/w_{total\ PAAG}$] of a N-hydroxyethyl acrylamide (HEA) side chain, ii) mixing the components of i) thereby achieving the composition.

In another embodiment, the invention relates to a process for making the composition, consisting of the steps of: i) providing stem cells, a cell culture medium and a polyacrylamide hydrogel (PAAG), wherein the PAAG contains less than 0.02% $w_{monomer}/w_{total\ PAAG}$] of a N-hydroxyethyl acrylamide (HEA) side chain, ii) mixing the components of i) thereby achieving the composition.

In one embodiment, the invention relates to a process wherein the PAAG does not contain a HEA side chain.

In one embodiment, the invention relates to a process wherein the stem cells are selected from at least one of embryonic (or genuine) stem cells or adult stem cells.

In a preferred embodiment, the invention relates to a process wherein the stem cells are selected from at least one of progenitor type stem cells, embryonic stem cells or induced pluripotent stem cells.

In yet a preferred embodiment, the invention relates to a process wherein the stem cells are selected from at least one of progenitor type stem cells, or induced pluripotent stem cells.

In an even more preferred embodiment, the invention relates to a process wherein the stem cells are mesenchymal stem cells.

In an aspect, the invention relates to a composition obtainable by the process of the invention.

In an embodiment, the invention relates to a composition obtained by the process of the invention.

In a further aspect, the invention relates to a composition according to the invention for use in medicine.

In one embodiment, the invention relates to a composition for use in medicine in a mammal.

In a further embodiment, the invention relates to a composition for use in medicine in a mammal wherein the mammal is selected from a human, a racing mammal or a companion mammal.

In a further embodiment, the invention relates to a composition for use in medicine in a mammal, wherein the stem cells are selected from at least one of progenitor type stem cells, embryonic stem cells or induced pluripotent stem cells.

In a further embodiment, the invention relates to a composition for use in medicine in a mammal wherein, the stem cells are mesenchymal stem cells.

In a further aspect, the invention relates to a composition according to the invention, for use in prevention and/or treatment of tendon injury in a mammal.

In a further embodiment, the invention relates to a composition according to the invention, for use in prevention and/or treatment of tendon injury in a mammal, wherein the mammal is selected from a human, a racing mammal or a companion mammal.

In an embodiment, the invention relates to a composition according to the invention, for use in prevention and/or treatment of tendon injury in a mammal, wherein the tendon injury is selected from one or more of trauma (injury), rupture (burst), tearing (by pressure) or ulcerative inflammation resulting in tissue weakness. Ulcerative inflammation is present when there has been a development of an ulcer over an area of inflammation thereby resulting in tissue weakness. Trauma is also known as injury and is a physiological wound caused by an external source.

In a further embodiment, the invention relates to a composition according to the invention, for use in prevention and/or treatment of tendon injury in a mammal wherein the tendon injury is selected from one or more of tendinitis, tendinosis or tendinopathy. Tendinitis means inflammation of a tendon. Tendinitis (also tendonitis), is a type of tendinopathy often confused with the more common tendinosis, which has similar symptoms but requires different treatment. Tendinosis, sometimes called chronic tendinitis, tendinosus, chronic tendinopathy, or chronic tendon injury, is damage to a tendon at a cellular level (the suffix "osis" implies a pathology of chronic degeneration without inflammation). It is thought to be caused by microtears in the connective tissue in and around the tendon, leading to an increase in tendon repair cells.

Tendinopathy is a general term for tendon damage involving overuse, microtears, and collagen degeneration, manifested by inflammation, pain, and weakness.

In a further embodiment, the invention relates to a composition according to the invention, for use in prevention and/or treatment of tendon injury in a mammal, wherein the stem cells are selected from at least one of progenitor type stem cells, embryonic stem cells or induced pluripotent stem cells.

In a further embodiment, the invention relates to a composition according to the invention, for use in prevention and/or treatment of tendon injury in a mammal, wherein the stem cells are mesenchymal stem cells.

In a further embodiment, the invention relates to a composition according to the invention, for use in prevention and/or treatment of tendon injury in a mammal, wherein the racing mammal to be treated is a horse.

In a further embodiment, the invention relates to a composition according to the invention, for use in prevention and/or treatment of tendon injury in a mammal wherein the tendon or tendons which is/are to be injected is the deep digital flexor tendon, the superficial digital flexor tendon or peritendinous tissues.

In a further embodiment, the invention relates to a composition according to the invention, for use in prevention and/or treatment of tendon injury in a mammal, wherein the ligament or ligaments which is/are to be injected is selected from one or more of the suspensory ligament, extensor branch of suspensory ligament, superficial distal sesamoidean ligament, tarsocrural lateral collateral ligament or periligamentous tissues.

In a further embodiment, the invention relates to a composition according to the invention, for use in prevention and/or treatment of tendon injury in a mammal, wherein the mammal to be treated is a human.

In a further embodiment, the invention relates to a composition according to the invention, for use in prevention and/or treatment of tendon injury in a mammal, wherein the tendon or tendons which is/are to be injected is selected from one or more of the achilles tendon, biceps tendon, patellar tendon, quadriceps tendon or the tendon/tendons of the planta pedis or rotator cuff.

In a further embodiment, the invention relates to a composition according to the invention, for use in prevention and/or treatment of tendon injury in a mammal, wherein the ligament or ligaments which is/are to be injected is selected from one or more of the anterior cruciate ligament, posterior cruciate ligament, collateral ligament or the ligament/ligaments of the planta pedis or rotator cuff.

In a further embodiment, the invention relates to a composition according to the invention, for use in prevention and/or treatment of tendon injury in a mammal, wherein the companion mammal to be treated is a dog.

In a further embodiment, the invention relates to a composition according to the invention, for use in prevention and/or treatment of tendon injury in a mammal, wherein the tendon or tendons which is/are to be injected is selected from one or more of the shoulder joint tendon, achilles tendon or common calcaneal tendon.

In a further embodiment, the invention relates to a composition according to the invention, for use in prevention and/or treatment of tendon injury in a mammal, wherein the ligament or ligaments which is/are to be injected is selected from one or more of the shoulder joint ligament, anterior cruciate ligament or posterior cruciate ligament.

In another aspect, the invention relates to a composition according to the invention, for use in prevention and/or treatment of arthritis in a mammal.

Arthritis is a group of conditions involving damage to the joints of the body i.e. pain caused by inflammation and cartilage destruction. There are over 100 different forms of arthritis. The most common form, osteoarthritis (degenerative joint disease) is a result of trauma to the joint, infection of the joint, or age. Other arthritis forms are rheumatoid arthritis, psoriatic arthritis, and related autoimmune diseases. Septic arthritis is caused by joint infection.

Osteoarthritis (OA) is a painful, debilitating joint disease with no known cure. It is characterized by heat, pain, swelling, crepitus (a crackling, crinkly, or grating feeling or sound under the skin), and a decreased range of motion in affected joints. In humans it affects the hands, knees, hips, spine and other joints. Horses suffer from joint osteoarthritis in primarily coffin, pastern, fetlock, carpal and stifle joints, and the incidence is dependent on age, weight, frequency and nature of physical actiivity and breed.

Rheumatoid arthritis (RA) is a long-lasting autoimmune disorder that primarily affects joints.

Lupus or lupus erythematosus is a name given to a collection of autoimmune diseases in which the human immune system becomes hyperactive and attacks normal, healthy tissues, such as joints.

Gout (also known as podagra when it involves the joint at the base of the big toe) is usually characterized by recurrent attacks of inflammatory arthritis—a red, tender, hot, and swollen joint.

Regardless of the type of arthritis, the common symptoms for all arthritis disorders include varied levels of pain, swelling, joint stiffness and sometimes a constant ache around the joint(s). The major complaint by individuals who have arthritis is joint pain. Pain is often constant and may be localized to the joint affected. The pain from arthritis occurs due to inflammation that occurs around the joint, damage to the joint from disease, daily wear and tear of joint, muscle strains caused by forceful movements against stiff, painful joints and fatigue.

In another embodiment, the invention relates to a composition according to the invention, wherein the mammal is selected from a human, a racing mammal or a companion mammal.

In another embodiment, the invention relates to a composition according to the invention, wherein the arthritis is selected from osteoarthritis (OA), rheumatoid arthritis (localised autoimmune disease with severe inflammation and cartilage destruction and warm, swollen, painful joints), lupus (generalised autoimmune disease with joint pain and swelling), or gout (attacks of a red, tender, hot, and swollen joint due to uric acid crystals).

In another embodiment, the invention relates to a composition according to the invention, wherein the stem cells are selected from at least one of progenitor type stem cells, embryonic stem cells or induced pluripotent stem cells.

In another embodiment, the invention relates to a composition according to the invention, wherein the stem cells are mesenchymal stem cells.

In another embodiment, the invention relates to a composition according to the invention, wherein the racing mammal to be treated is a horse.

In another embodiment, the invention relates to a composition according to the invention, wherein the joint or joints which is/are to be injected is one or more of the fetlock, coffin, pastern, stifle, and/or knee joint of the hind legs.

In another embodiment, the invention relates to a composition according to the invention, wherein the companion mammal to be treated is a dog.

In another embodiment, the invention relates to a composition according to the invention, wherein the joint or joints which is/are to be injected is one or more of the elbow of the front leg or the knee or hip joint of the hind legs.

In another embodiment, the invention relates to a composition according to the invention, wherein the mammal to be treated is a human.

In another embodiment, the invention relates to a composition according to the invention, wherein the joint or joints which is/are to be injected is one or more of the knee, hip, elbow, the metacarpal-phalangeal and interphalangeal joints in hands and feet, the sesamoid joint and/or the temporomandibular joint.

In an aspect, the invention relates to a composition according to the invention, for use in prevention and/or treatment of arthropathy or joint disease in a mammal.

Arthropathy in a mammal is a general term for joint pain and/or instability, of which arthritis caused by inflammation of the synovial membrane and destruction of the cartilage is the most common.

In an embodiment, the invention relates to a composition according to the invention, for use in prevention and/or treatment of arthropathy in a mammal, wherein the mammal is selected from a human, a racing mammal or a companion mammal.

In an embodiment, the invention relates to a composition according to the invention, for use in prevention and/or treatment of arthropathy in a mammal, wherein the arthropathy is selected from reactive arthropathy, enteropathic arthropathy, crystal arthropathy, diabetic arthropathy and/or neuropathic arthropathy.

In an embodiment, the invention relates to a composition according to the invention, for use in prevention and/or treatment of arthropathy in a mammal, wherein the racing mammal to be treated is a horse.

In an embodiment, the invention relates to a composition according to the invention, for use in prevention and/or treatment of arthropathy in a mammal, wherein the joint or joints which is/are to be injected is one or more of the fetlock, coffin, pastern, stifle, and/or knee joint of the hind legs.

In an embodiment, the invention relates to a composition according to the invention, for use in prevention and/or treatment of arthropathy in a mammal, wherein the mammal to be treated is a human.

In an embodiment, the invention relates to a composition according to the invention, for use in prevention and/or treatment of arthropathy in a mammal, wherein the joint or joints which is/are to be injected is one or more of the knee, hip, elbow, the metacarpal-phalangeal and interphalangeal joints in hands and feet, the sesamoid joint and/or the temporomandibular joint.

In an embodiment, the invention relates to a composition according to the invention, for use in prevention and/or treatment of arthropathy in a mammal, wherein the companion mammal to be treated is a dog.

In an embodiment, the invention relates to a composition according to the invention, for use in prevention and/or treatment of arthropathy in a mammal, wherein the joint or joints which is/are to be injected is one or more of the elbow of the front leg or the knee or hip joint of the hind legs.

In an embodiment of the invention, the composition of the invention is provided in a pre-packaged sterile syringe.

Preparation of the Polyacrylamide Hydrogel (PAAG)

The hydrogel may be prepared as described in WO 02/16453, hereby incorporated by reference. In the following, the polyacrylamide hydrogel may be abbreviated PAAG.

The hydrogel may comprise any embodiment of the hydrogel as described in WO 02/16453 and WO 2012/123385. Preferably, the hydrogel comprises 0.5 to 25% by weight polyacrylamide, based on the total weight of the hydrogel. The hydrogel typically further comprises at least 75% by weight pyrogen-free water or saline solution, preferably pyrogen-free water.

The hydrogel is obtainable by combining acrylamide and cross-linking monomers, initiating polymerisation by radical initiation; and washing with pyrogen-free water or saline solution, the combining being in amounts and the washing being such as to give about 0.5 to 25% by weight polyacrylamide, based on the total weight of the hydrogel. The hydrogel thus obtained is both biostable and biocompatible, and is not resorbed by the body.

Typically, the hydrogel is obtained by combining acrylamide and cross-linking agent, such as N,N'-methylene bis-acrylamide, in a molar ratio of 150:1 to 1000:1. The cross-linking agent, such as N,N'-methylene bis-acrylamide, serves to provide cross-linking between polymer chains and the molar ratio may be varied to provide various cross-linking densities of the hydrogel. The conditions for obtaining the hydrogel may be modified according to, for instance, the nature of e.g. the joint, tendon, ligament, tissue into which the hydrogel is intended to be injected. The desired rheological properties, such as elasticity, may be controlled at least in part by the solid weight content of the hydrogel. The hydrogel of the invention comprises about 0.5 to 25% by weight polyacrylamide, based on the total weight of the hydrogel. In suitable embodiments of the invention, the hydrogel comprises less than 15% by weight polyacrylamide, based on the total weight of the hydrogel, preferably less than 10% by weight, more preferably less than 7.5% by weight, even more preferably less than 5%, most preferably less than 3.5% by weight polyacrylamide, based on the total weight of the hydrogel. In a preferred embodiment, the hydrogel of the invention has a solid weight contents of about 0.5 to 20% by weight polyacrylamide, based on the total weight of the hydrogel, such as about 0.5 to 15% by weight, such as about 0.5 to 10% by weight, such as about 0.5 to 5% by weight, such as about 1.0 to 5% by weight, such as about 1.5 to 5% by weight, such as about 2.0 to 5% by weight, such as about 2.5 to 5% by weight, such as about 3.0 to 5% by weight, such as about 3.5 to 5% by weight, such as about 4.0 to 5% by weight, such as about 1.0 to 4.5% by weight, such as about 1.5 to 4.5% by weight, such as about 1.5 to 4% by weight, such as about 1.5 to 3.5%, such as about 2.0 to 3.5% by weight, such as about 2.0 to 3.0% by weight, such as about 2.2 to 2.8% by weight. In a more preferred embodiment, the hydrogel of the invention has a solid weight contents of about 2.0 to 3.0% by weight of polyacrylamide, based on the total weight of the hydrogel. In an even more preferred embodiment, the hydrogel of the invention has a solid weight content of about 2.2 to 2.8% by weight polyacrylamide, based on the total weight of the hydrogel. In the present context, the term "solid weight content" is used interchangeably with the term "dry matter content".

The combining involves the combining of the component reagents acrylamide and cross-linking agent, such as N,N'-methylene bis-acrylamide, typically degassed and typically in a manner to minimise operator contact. The reagent components may optionally be combined previously to form an inert mixture. An inert mixture is one wherein no chemical reaction proceeds among the component reagents. The combining involves combining acrylamide, cross-linking agent, such as N,N'-methylene-bis-acrylamide, and a radical initiator component to initiate polymerisation. In a suitable embodiment, an inert premixture of acrylamide, cross-linking agent, such as N,N'-methylene-bis-acrylamide, and N,N,N',N'-tetramethylene-ethylene-diamine (TEMED) is combined with an ammonium persulfate (AMPS) initiator solution. However, the components may be combined as singularities or as alternative plural premixtures.

Acrylamide and cross-linking agent, such as N,N'-methylene-bis-acrylamide, are suitably combined in a molar ratio of about 150:1 to 1000:1, typically about 150:1 to 900:1, preferably about 175:1 to 800:1, more preferably about 200:1 to 600:1, most preferably from 250:1 to 600:1. As shown in Tables 2 and 3, hydrogels of differing solid-weight content and rheological properties may be controllably prepared. The hydrogel having the desired rheological characteristics has been obtained by combining acrylamide and N,N'-methylene-bis-acrylamide in a ratio of about 250:1, about 260:1, about 270:1, about 280:1, about 290:1, about 300:1, about 310:1, about 320:1, about 330:1, about 340:1, about 350:1, about 360:1, about 370:1, about 380:1, about 390:1, about 400:1, about 410:1, about 420:1, about 430:1, about 440:1, about 450:1, about 460:1, about 470:1, about 480:1, about 490:1 and about 500:1.

Particularly in the embodiment wherein the hydrogel is injected into a joint, tendon or ligament the elasticity of the hydrogel is of great relevance. In a preferred embodiment, the hydrogel of the invention has an elasticity modulus of about 1 to 200 Pa, such as about 2 to 175 Pa, typically about 5 to 150 Pa, such as about 10 to 100 Pa, such as about 20 to 100 Pa, such as about 30 to 100 Pa, such as about 40 to 100 Pa, such as about 50 to 100 Pa, such as about 50 to 95 Pa, such as about 55 to 95 Pa, such as about 55 to 90 Pa, such as about 15 to 95 Pa, such as about 20 to 85 Pa, such as bout 25 to 80 Pa, such as about 30 to 75 Pa, such as 30 to 65 Pa, such as 30 to 55 Pa, such as 30 to 58 Pa, such as 33 to 55 Pa such as about 35 to 70 Pa, such as about 40 to 65 Pa, such as about 45 to 60 Pa, such as about 50 to 55 Pa. In an even more preferred embodiment, the hydrogel of the invention has an elasticity modulus of about 33 to 55 Pa or about 55 to 90 Pa. Persons skilled in the art will be aware of how to obtain a hydrogel with a suitable elasticity for the intended use. See also the examples below, which describe preparation of hydrogels with low, medium and high elasticity.

The elasticity modulus of the PAAG is of great importance to the ability of stem cells to survive and divide. It is important that the PAAG is stable, physically and chemically after formation. In fact, degradation products from the polymerization process (sulphate) is below 4 ppm and once the polymerization process is to an end, the PAGG remains physically and chemically stable, also after having been injected into tissue.

In tissue, the gel also remains chemically and physically stable, and does not release leachable products, as it does not degrade in tissue at all—it is permanent. Therefore, the degradability of the PAAG upon injection into a tissue is an important factor of the hydrogel of the invention too, to secure stable growth of stem cells. The PAAG hydrogel does not degrade over time (i.e. it is permanent) and it allows fibre and vessel ingrowth. Thus, the PAAG hydrogel of the present invention is non-degradable, safe to use and non-toxic i.e. it does not release toxic components over time.

The hydrogel comprises at least 75% by weight pyrogen-free water or saline solution, preferably pyrogen-free water. In a suitable embodiment of the invention, the hydrogel comprises at least 80% by weight pyrogen-free water or saline solution, preferably at least 85%, more preferably at least 90%, even more preferably at least 95% by weight pyrogen-free water or saline solution.

A suitable saline solution has an osmolarity similar to that of interstitial fluid. Suitable saline solutions include but are not limited to the group comprising 0.25-1% aqueous sodium chloride, a Ringer-Lockart solution, an Earle solution, a Hanks solution, an Eagle medium, a 0.25-1% glucose solution, a potassium chloride solution, and a calcium chloride solution. In a preferred embodiment, the saline solution is a 0.8-1% aqueous sodium chloride solution, such as a 0.8, 0.9 or 1% aqueous sodium chloride solution, most preferably about 0.9% aqueous sodium chloride.

As will be obvious to the person skilled in the art, in the embodiment wherein saline solution is used either for the preparation of the PAAG and/or for the washing of the PAAG, the solid-weight content of the PAAG will be higher than the contribution made by the polyacrylamide, but typically not more than an additional 1%.

In a particularly suitable embodiment of the invention, the hydrogel comprises about 2.5% by weight polyacrylamide, based on the total weight of the hydrogel and about 97.5% pyrogen-free water.

Pyrogen-free water or saline solution is used for washing the hydrogel in a washing process. The washing process serves, in part, to remove all but trace amounts of the monomers acrylamide and cross-linking agent, such as N,N'-methylene-bis-acrylamide. These monomers are toxic to the patient as well as detrimental to the stability of the hydrogel. The washing process is preferably such that the concentrations of the remaining monomers acrylamide and cross-linking agent, such as N,N'-methylene-bis-acrylamide, are below 50 ppm, more preferably below 40 ppm, such as below 30 ppm, most preferably below 20 ppm, typically below 10 ppm, particularly preferably below 5 ppm or even more preferably below 1.5 ppm.

Cross-Linking Agents

The hydrogel according to the present invention may contain a cross-linking agent selected from the group consisting of N,N'-methylene-bis-acrylamide, N,N'-ethylene-bis-acrylamide, ethylene-bis (oxyethylene nitril)-tetracetic oxide, ethylene-bis-(oxyethylene nitril) tetracetic acid, and mixtures thereof. In one embodiment, said cross-linking agent is selected from the group consisting of N,N'-methylene-bis-acrylamide, N,N'-ethylene-bis-acrylamide, and mixtures thereof. In a further embodiment, said cross-linking agent is N,N'-methylene-bis-acrylamide.

It should be noted that embodiments and features described in the context of one of the aspects of the present invention also apply to the other aspects of the invention.

All references cited in the present application, are hereby incorporated by reference in their entirety.

The invention will now be described in further detail in the following non-limiting examples.

EXAMPLES

Example 1—Preparation of Hydrogel

Preparation of Hydrogel:

The PAAG is a polyacrylamide gel manufactured by a polymerisation of the monomers of acrylamide (AM) and N,N'-methylene-bis-acrylamide (bisAM). N-hydroxyethyl acrylamide (HEA) may also be added to the mixture. The finished product may have different elasticity modules.

The hydrogel typically contains approximately 95% water. The concentration of the residual monomers acrylamide and N,N'-methylene-bis-acrylamide after washing process step has been shown to be less than 10 ppm and is adequate for the desired stability of the final product, often less than 5 ppm.

The finished product must conform with respect to pH, absence of heavy metals, refractive index, stability, absence of pyrogens, and must be sterile, practically inert, and be substantially free of monomers. The pH of the finished product is about 7-9, such as preferably 7.3-8.5, such as about 8.2.

Preparation 1.1

The synthetic preparation suitably involves the following operations:
1. Two mixtures, A1 and A2, are prepared. A1 comprises water, acrylamide, N,N'-methylene-bis-acrylamide, N,N,N',N'-tetramethylene-ethylene-diamine (TEMED). A2 comprises water and ammonium persulfate;
2. The two mixtures are combined in the following ratio: 1990 mL of A1 and 10 mL of A2 and kept at 45° C. and degassed with nitrogen for 20 seconds;
3. The reaction mixture is cast into several 100 mL beakers;
4. Polymerisation is allowed to occur for 0.5 to 1.5 hours;
5. The gel is demolded;
6. Residual monomers are extracted and with equilibration in WFI water for 92 hours, changing the water several times, typically 8 times during the 92 hours;
7. The purified gels are homogenised by grinding with a vertically oscillating grid;
8. A syringe is filled with the homogenised gel material;
9. Autoclavation of the syringe A typical method for preparing the hydrogel may be summarised as:

Preparation 1.2

Process Summary

The gel is prepared by mixing an aqueous monomer solution of acrylamide (AM) and N,N'-methylene-bis-acrylamide (bisAM) as cross-linker with N,N,N',N'-tetramethylene ethylene diamine (TEMED) as co-initiator and ammonium persulfate (AMPS) as free-radical initiator (redox-system). By degassing a bulk solution with nitrogen, polymerisation starts. After final polymerisation the gel is transferred into a washing tank with net trays onto which the gel is placed. During water washing, the gel swells and monomer residues are extracted. The swollen gel is fed and evacuated in a filling unit having the gel delivered in a syringe, which is autoclaved. Two alternate formulations have been prepared, a lower- and a higher-end elasticity formulation.

TABLE 1

| Chemical constituent | lower end elasticity | higher end elasticity |
|---|---|---|
| acrylamide | 502 g | 547 g |
| N,N'-methylene-bis-acrylamide | 2.2 g | 4.6 g |
| TEMED | 3.0 g | 2.6 g |
| AMPS | 5.4 g | 5.0 g |
| Non-pyrogenic water | Add 10 litre | Add 10 litre |

The above are typical preparations of the hydrogel and may be adjusted within certain ranges.

Alternatively, the same raw material composition may be used for both lower end and higher end elasticity modulus as the reaction conditions may also be used to obtain difference in elasticity modulus instead of adjusting the dry matter content. Both methods are suitable in the present invention.

Preparation 1.3

Polyacrylamide Formulations From Inline Cross-Linking Process

A particularly interesting method of preparing the hydrogels of the invention involves an inline cross-linking process. Two individual and eventually degassed flows, one being a pre-mix of acrylamide, N,N'-methylene-bis-acrylamide (the cross-linker) and TEMED, the other being the AMPS initiator solution, are pumped into a static mixer for mixing, chemical initiation and subsequent extrusion downstream into a pipe reactor made of Teflon or steel in which the polymerisation occurs. Washing of the gel is simplified due to high surface area of gel from reactor.

By selecting monomer, cross-linker and initiator concentrations and their relative molar ratios, and by regulating the two flow rates and the polymerisation temperatures, it is possible to produce gels that are varying in degree of crosslinking and in solids content.

Preparation 1.4

The reagents were combined in ratios described in Tables 2, 3 and 4, and washed as described in the Tables (with pyrogen-free water unless indicated otherwise) to give low, medium, and high elasticity formulations. Hydrogels with solid weight contents between 0.5 and 25% polyacrylamide were prepared.

TABLE 2

Process parameters and features of resulting gel: low elasticity formulations

|  | Iv1 | Iv2 | Iv3 | Iv4 | Iv5 | Iv6 | Iv7 [d] | Iv8 [e] |
|---|---|---|---|---|---|---|---|---|
| washing time (hrs) | a) | 19.5 | 73.75 | 92 | 94.3 | 72.8 | 93.6 | 93.9 |
| dry matter [i] (%) | 2.55 | 2.08 / 2.36 | 2.63 / 2.58 / 2.09 | 2.87 / 2.67 | 2.89 / 2.82 | 3.15 / 2.90 | 3.68 / 3.57 | 3.17 / 3.52 |
| molar ratio AM:bisAM | b) | 976 | 700 | 488 | 366 | 3239 | 488 | 488 |
| molar ratio AM + bisAM:TEMED | 252 | 252 | 253 | 251 | 252 | 249 | 252 | 252 |
| molar ratio AM + bisAM:AMPS | 298 | 299 | 298 | 298 | 298 | 299 | 298 | 298 |
| residual monomer in ppm | c) | 89 | 5 | 2.97 | 2 | 5 | 1.4 | 0.97 |
| elasticity G' in Pa | 0.16 | 5.23 | 14.3 / 20.1 | 26.6 | 57.0 5 | 71.7 | 39.2 | 28.5 |
| gelation time (min) | liquid | highly viscous liquid | 12 | 2 | 2 | 2 | 2.5 | 2.5 |

|  | Iv9 | Iv10 | Iv11 | Iv11 | Iv12 |
|---|---|---|---|---|---|
| washing time (hrs) | 121 | 96.4 |  |  |  |
| dry matter (%) | 2.18 | (5.10)[f] | (10.2)[f] | (10.1)[f] | (20.2)[f] |
| molar ratio AM:bisAM | 701 | 701 | 488 | 488 | 488 |
| molar ratio AM + bisAM:TEMED | 252 | 252 | 252 | 504 | 2016 |
| molar ratio AM + bisAM:AMPS | 298 | 298 | 298 | 596 | 2385 |
| residual monomer in ppm |  | 0.97 |  |  |  |
| elasticity G' in Pa | 28.5 | 11.1 | (911)[g] | (1240)[g] | (9460)[g] |
| gelation time (min) |  | 3.17 | 0.00 | 1.21 | 3.5 [h] | a) material was liquid so washing was a dilution
b) infinite
c) Since washing was not an extraction but a dilution, the residual monomer was merely decreased by the dilution factor (508 ppm to 254 ppm).
[d] casting and washing done using 0.9% NaCl aqueous solution
[e] casting with water; washing done using 0.9% NaCl aqueous solution
[f] pre-wash values - washing typically reduces value by 30-55%
[g] pre-wash values - washing typically reduces value by 20-40%
[h] highly notch sensitive
[i] variations in values may be due to measurement performance techniques or to location in the batch from which sample was taken

TABLE 3

Process parameters and features of resulting gel: medium elasticity formulations

|  | mv1 | mv2 | mv3 | mv4 | mv5 |
|---|---|---|---|---|---|
| washing time (hrs) | 97 | 211.5 | 96 | 94.8 | 90.3 |
| dry matter (%) | 3.14 | 2.49 | 3.25 | 3.29 | 3.22 |
| molar ratio AM:bisAM | 310 | 310 | 290 | 289 | 289 |
| molar ratio AM + BISAM:TEMED | 252 | 252 | 252 | 251 | 252 |
| molar ratio AM + BISAM:APS | 299 | 299 | 299 | 299 | 299 |
| residual monomer in ppm | 1.6 |  | 1.5 |  |  |
| elasticity G' in Pa | 108.5 |  | 129 | 133.5 |  |
| gelation time (min) | 2.5 | 2.5 | 2.18 |  |  |

TABLE 4

Process parameters and features of resulting gel: high elasticity formulations

|  | hv1 | hv2 | hv3 | hv4 | hv5 |
|---|---|---|---|---|---|
| washing time (hrs) | 119.5 | 516 | 122 | 95.5 | 116.7 |
| dry matter (%) | 3.47 | 2.5 | 3.56 | 3.83 | 3.42 |
| molar ratio AM:bisAM | 260 | 260 | 260 | 260 | 260 |
| molar ratio AM + bisAM: TEMED | 315 | 315 | 604 | 313 | 314 |
| molar ratio AM + bisAM: AMPS | 376 | 376 | 755 | 375 | 376 |
| residual monomer in ppm | 0.2 | | | | |
| elasticity G' in Pa | 343 | 274 | | 314.5 | |
| gelation time (min) | 2.18 | 2.18 | 7.5 | | |

Example 2—In Vitro Experiments

Example 2 presents data of in vitro studies on mesenchymal stem cell viability, proliferation and migration onto tendon tissue and whether it induces a proinflammatory change in the phenotype of the stem cells.

Example 2.1—Preparation of Mesenchymal Stem Cells (MSC)

Source of MSCs:

Equine bone marrow-derived MSCs (n=3) were derived from bone marrow aspirated from horses undergoing stem cell treatment for forelimb tendon injuries. Briefly, the mononuclear cell population from the buffy layer of 10 ml bone marrow aspirate was seeded into cell culture plastic flasks in D10 medium (Dulbecco's Modified Eagle Medium, DMEM, supplemented with fetal bovine serum (10% v/v), 100 U/ml penicillin, and 100 U/ml streptomycin). The plastic adherent stem cell population was expanded in culture, detached from the plastic surface and the cells between passage 0 and 2 (P0 to P2) were resuspended in Bambanker™ cell cryostorage medium and then stored in liquid nitrogen or at −80° C. until used for experiments. For the experiments described, cells from these frozen stocks were expanded in plastic flasks in D10 medium to obtain required numbers. For experiments, cells expanded to between P2-4 were used. The multipotency of cells prepared by this method has been described earlier by trilineage ability, fibroblastic morphology and colony forming unit-fibroblast (CFU-F) assay by Smith R K, Korda M, Blunn G W, Goodship A E.

Example 2.2—Preparation of MSCs Encapsulated in PAAG, Integrity and Breakdown

Figure 1:
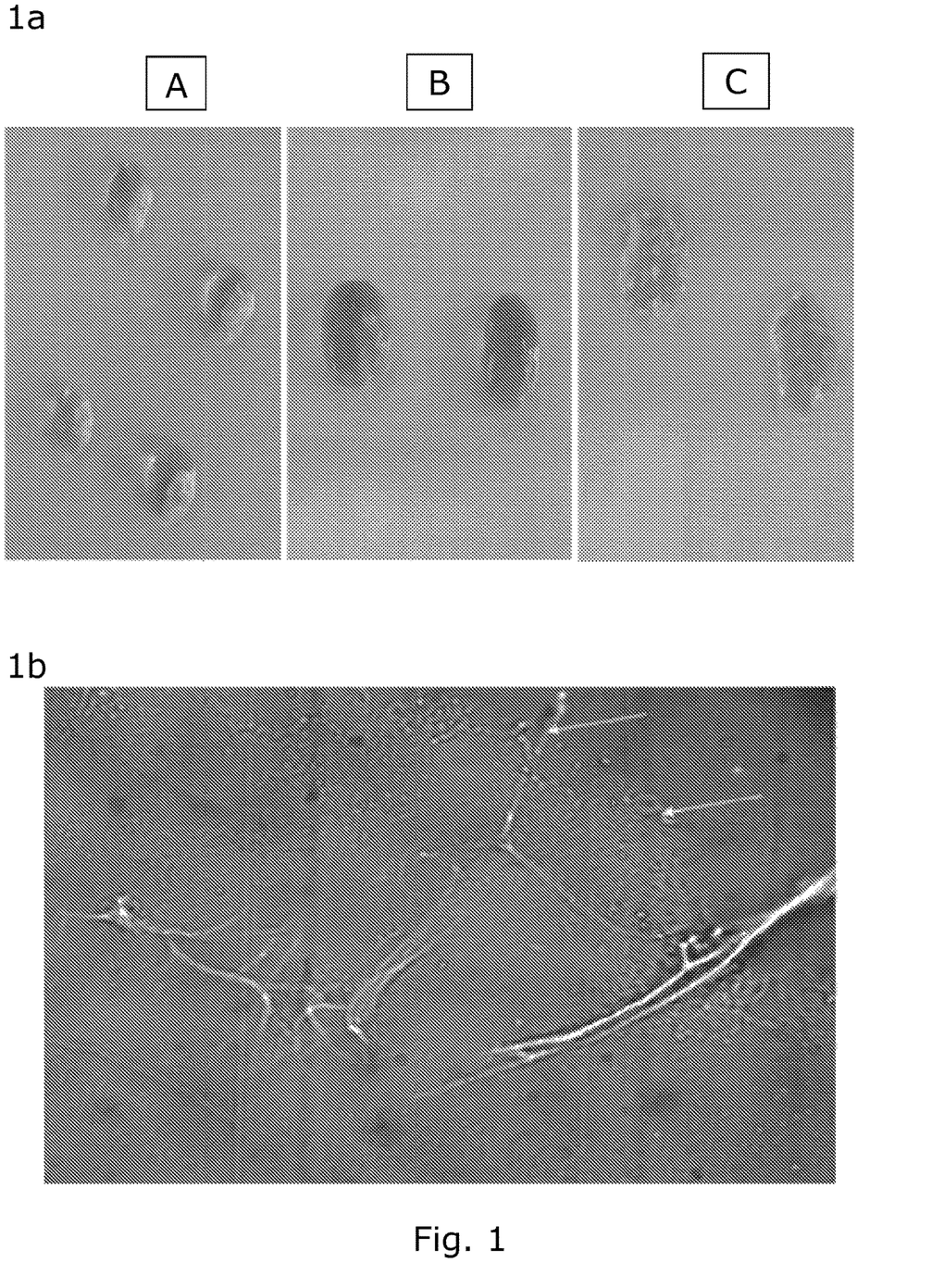
FIG. 1a shows naked eye appearance of PAAG beads at creation (A), after 5 days (B) and after 10 days. Polymer integrity and breakdown is visible.
FIG. 1b shows low power brightfield microscope image (×200) of a PAAG bead with encapsulated MSCs (arrows) after 24 h culture. The MSCs appear as dark spots within the PAAG (black arrows).

PAAG Source:

PAAG were provided by Contura International A/S, Denmark, supplied as pre-packaged, 1 ml sterile syringes (Arthramid® gel). The PAAG was prepared as disclosed in example 2. The gel was extruded into sterile culture dishes and a specific volume of cell suspension was added to the gel (40 μL comprising about 500 cells). This results in expansion of the polymer as the liquid is absorbed and distributed throughout the polymer. This was necessary in order to increase the volume of the Arthramid® gel to efficiently re-suspend the cells throughout a droplet. Approximately 50 μl Arthramid® polymer was pipetted directly onto the desired tissue culture surface (i.e. the culture dish) followed by the addition of 40 μl comprising about 500 cells of MSC-cell suspension for viability experiments. Resultantly, MSCs Encapsulated in PAAG is the Outcome PAAG Integrity and Breakdown:

PAAG integrity and breakdown was investigated by visual inspection and the results are shown in FIG. 1a. PAAG was extruded in beads from the sterile syringes (Arthramid® gel) and investigated. The beads are approximately 5 mm in diameter: A) PAAG beads are shown within 5 min after the PAAG was extruded from the syringe to demonstrate their physical strength and clarity; B) PAAG beads that were placed in D10 medium are shown after 5 days in a tissue culture incubator; C) PAAG beads that were placed in D10 medium are shown after 10 days in a tissue culture incubator (i.e. a cell culture incubator with a humidified atmosphere of 5% CO2 in air at 37° C.). The PAAG beads were observed to remain physically intact for the first 5 days and thereafter slowly disintegrated as can be seen in the difference in their physical appearance between 5 and 10 days going from a smoothly defined surface to one that was more ruffled at the edges. At 10 days the PAAG polymer beads had strands of polymer which were observed as fine string-like extensions that were detectable around the bead and as free strands in the culture media for the duration of all experiments. However, it should be noted that a small amount of strand, formation (signs of disintegration) was observed under low power light microscopy as early as 24 h in culture. This is demonstrated in FIG. 1b that shows a low power brightfield microscope image of a PAAG bead with encapsulated MSCs after 24 h culture. The brightfield microscope was an Olympus CX41. Examples of fine strands of the polymer are arrowed trailing off from the edge of the bead which is to the left of the image. These increase with culture time. The MSCs appear as dark spots within the PAAG.

Figure 2:
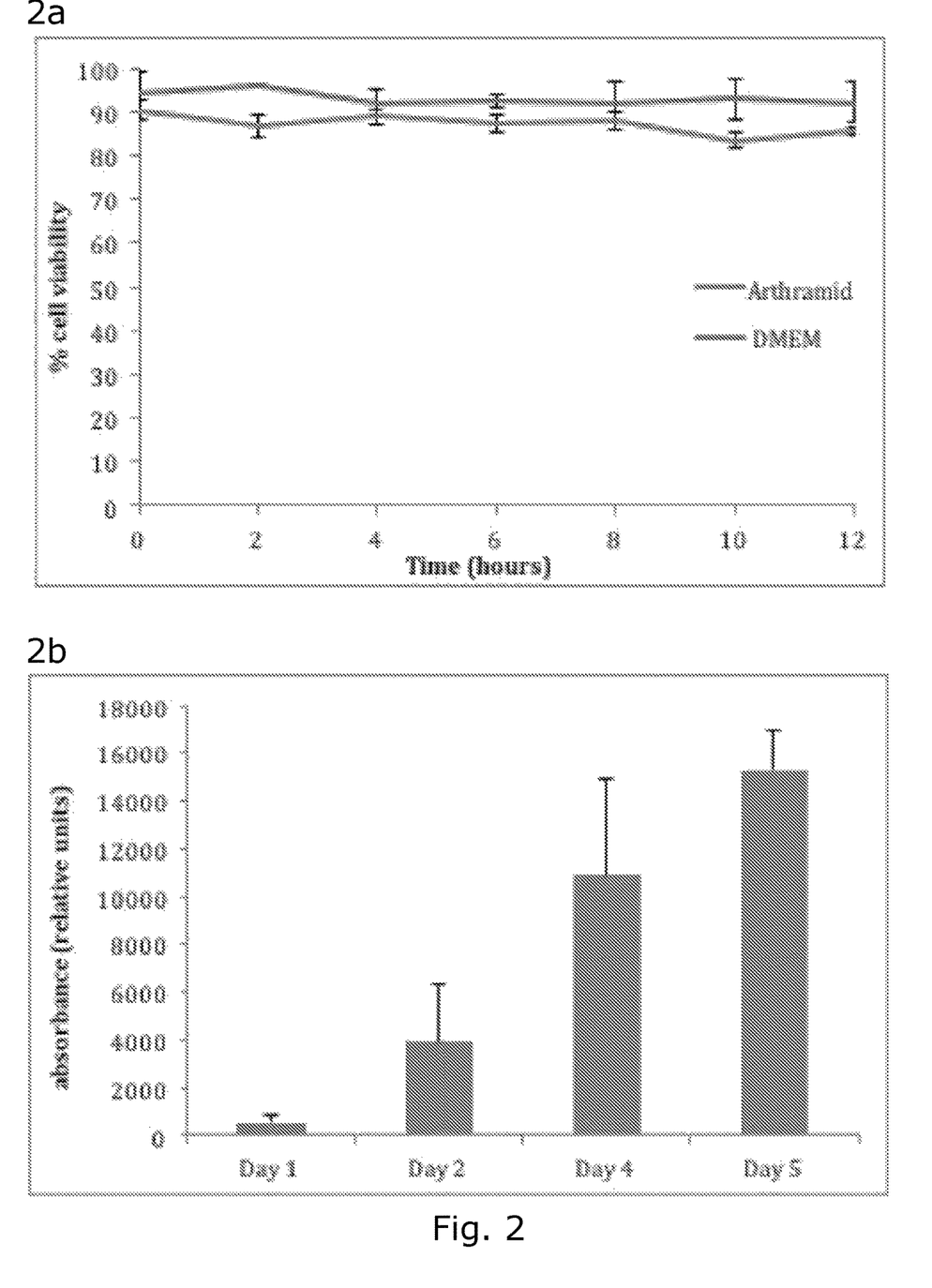
FIG. 2a shows the 12 h viability of MSCs in PAAG (lover curve) compared to control (upper curve). 90% of cells remain viable.
FIG. 2b shows proliferation of MSCs in PAAG assessed using the alamarBlue® assay. The proliferation of the MSCS shows an exponential increase in cell numbers over 5 days

Example 2.3—Viability, Proliferation and Pro-Inflammatory Response of MSCs in PAAG Viability of MSCs Encapsulated in PAAG:

The viability of MSCs encapsulated in PAAG compared to control was investigated and the results are shown in FIG. 2a. The figure shows MSCs re-suspended in D10 only (DMEM, upper curve, control experiment) or encapsulated in PAAG beads placed in D10 medium (Arthramid, lover curve) assayed for viability (live/dead assay) over 12 hours in culture i.e. time vs cell viability %. (data not shown). The percentage of cells alive was quantified using a cell vitality dye (live-dead assay) at the time points indicated. The cell vitality dye live-dead assay implies adding an equal volume of cell suspension to Trypan Blue dye (0.4%) and counting the cells under the microscope using a heatocytometer. The usual volume uses is 50 uL of celle suspension and 50 uL Trypan Blue. Viability assays using this method could not be performed on beads older than 12 h, as changes to the disintegrating polymer inhibited fluorescence of the cell vitality dye during microscopy. There was a small (approximately 5%) but significant decrease in the viability of cells in PAAG in comparison to cells suspended in D10 ($p<0.001$) immediately after the cells were suspended in the PAAG (time 0 mins). However, there was no further decrease in viability over the 12 h period with approximately 90% of cells remaining viable in the PAAG.

Proliferation of MSCs in PAAG:

FIG. 2b shows the results of the proliferation of MSCs in PAAG assessed using the alamarBlue® assay. PAAG beads containing 5,000 MSCs were cultured in D10 medium and the proliferation assay was performed at days 1 to 5 to quantitate the increase in the number of cells within the beads. The proliferation of the MSCs showed an exponential increase in cell numbers over 5 days which suggested an uninhibited ability of the cells to divide in PAAG. This rate of proliferation is comparable to that seen on tissue culture plastic.

Figure 3:
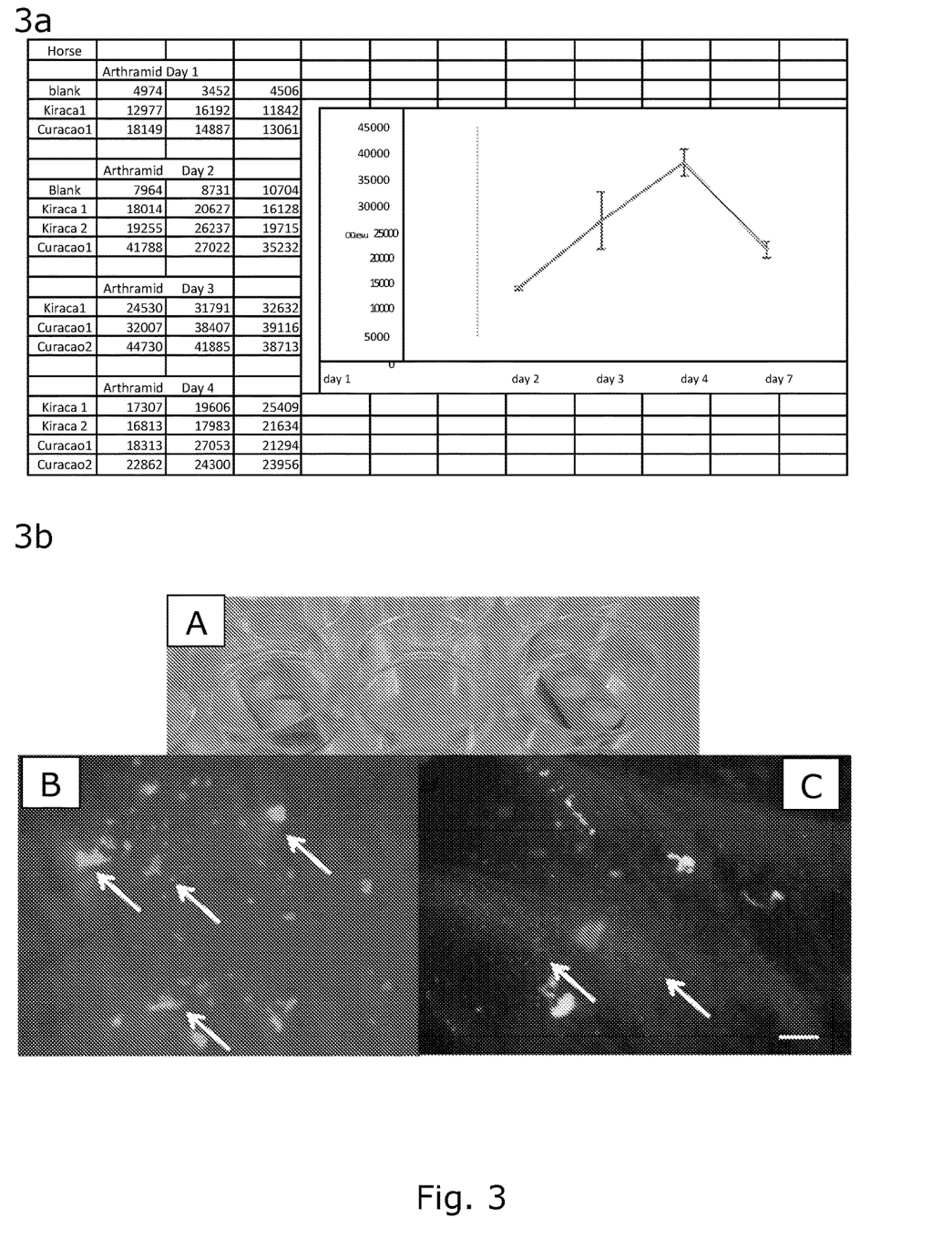

FIG. 3a shows a proliferation assay of MSCs encapsulated in PAAG readouts. These assays were performed using cells from different horses (two in this example are Kiraca, Curacao). The data are readouts from a fluorescence plate reader (Infinite M200 PRO fluorimeter, Tecan, UK) from which the proliferation curve was produced. Proliferation increased up to day 3, after which time the cell numbers became too large (confluent) on the culture dish and the proliferation dye concentration becomes saturated and cannot be read accurately (day 4 & day 7—data is not shown for day 7). The results surprisingly demonstrated that MSCs proliferate uninhibited in PAAG.

Induction of IL-1β in MSCs:

IL-1β was undetectable in the culture medium of MSCs-containing beads after 7 days (10 beads loaded with 35,000 cells each, in 1 ml D10), indicating surprisingly that PAAG does not stimulate a pro-inflammatory response in the suspended MSCs.

Example 2.4—Migration Ability of PAAG Encapsulated-MSCs Onto Tendon Matrix

FIG. 3b shows the migration ability of PAAG encapsulated-MSCs onto tendon matrix. A) Nonviable Native Tendon Matrices (NNTMs) were prepared from a deep digital flexor tendon of a horse by cutting small sections (2 cm long by 1 cm wide by 2 mm thick). These sections were then repeatedly subjected to a freeze-thaw cycle to kill all endogenous cells. The NNTM sections can be seen placed within a well of a multiwell tissue culture plate with two PAAG beads (gels) on top of each section. There are two multiwell tissue culture plates; one to the left in A and one to the right and each contain 2 sections with PAAG beads on each top. These beads contained MSCs labelled with the green fluorescent cell dye SPDiOC18. The tissue sections with the beads were then covered with D10 medium and co-cultured for 5 days to assess the ability of the PAAG encapsulated cells to migrate onto tendon matrix, prior to visualization with a fluorescent microscope.

B) Fluorescent microscopy images of the tendon sections after the remains of PAAG beads had been removed from the surface of the tendon sections. The viable fluorescent-labelled cells (arrows marking flourescent signal (appears as white signal here as figures are in black and white)) were observed to have adhered to the matrix of the tendon at 5 days. Because of the disintegration of the beads at 5 days it is not conclusive whether the cells in the NNTMs are because they have migrated out of the PAAG beads, or were released as the bead disintegrated. However, the result demonstrates that the cells are not inhibited from adhering to the tendon extracellular matrix after having been encapsulated within the PAAG hydrogel. The tendon matrix exhibits a background fluorescence which is seen as the lighter white background.

C) This tendon section is similar to B to show viable white cells (labelled MSCs) but in addition the tendon section has been stained with propidium iodide dye to show dead cells. Most of the dead cells were the non-viable resident tenocytes which can be recognized as lying in aligned rows in the tendon matrix.

Summary and Conclusions on the In Vitro Results

The results of the experiments discussed above in Example 2 surprisingly demonstrate that equine mesenchymal stem cells remain viable, proliferate and migrate when PAAG is used as a scaffold in equine tendon tissue. The gel does not induce a pro-inflammatory response based on undetectable levels of IL-1β. Hence, PAAG may be used as a scaffold in the repair of tendinopathy.

Example 3—In Vivo Experiments

Example 3 presents data on a clinical trial on the safety of the administration of PAAG into the anatomical structures frequently affected by naturally occurring tendinopathy in the horse. Further, an injection into the metacarpophalangeal joint was performed with MSCs vehiculated in plasma or PAAG, respectively.

Example 3.1—Safety of Injection of PAAG Demonstrated in a Clinical Trial

PAAG gel was provided in the form of sterile packaged 1 ml pre-loaded PAAG with a Luer-locking connector for hypodermic needle. Normal horses with no orthopaedic abnormalities and free of lameness were used for the clinical trial. The area to be implanted was examined ultrasonographically before administration. One dose of PAAG as provided by the manufacturer was administered in the central core of the following anatomical structures:

1. Mid third of the superficial digital flexor tendon (SDFT)
2. Mid third of the deep digital flexor tendon (DDFT)
3. Accessory ligament of the deep digital flexor tendon (ALDDFT)
4. Origin of the suspensory ligament (OSL)
5. Lateral branch of the suspensory ligament (LB), 1 cm proximal to the metacarpofalangeal joint.

A total of n=3 of each structure were included, a total of 18 injections were performed. A maximum of 2 structures were used on each experimental horse, using on each structure a different limb on each horse.

The anatomical location was aseptically prepared over injection site. The horse was lightly sedated and restrained. Local anaesthesia on the lateral palmar nerve or a lateral ring proximal to the injection site was performed previously to the administration. Injection was conducted with a 20 G 1.5 cm hypodermic needle under ultrasonographic guidance. On each injection 0.5 ml of the PAAG was administered. A distal limb padded bandage was placed and it was removed at each exam time. Bandages were maintained until day 3 post-implantation.

The monitorization of each patient included rectal temperature, contour of the limb, palpation of the injection area and presence of lameness at walk. Haematology and fibrinogen were measured before the injection and at day 3 and 7 post injection. Each exam was completed at 3 hours, 12 hours, and each following day until 7 days post administration. On each day post-administration an ultrasonographic exam of the injection site were performed until day 7. If a lesion or hypoechoic-anechoic image was obtained, ultrasonographic exam was repeated every 7 days until normality was regained.

A final phase will included the tracking of a mix of PAAG-MSCs. This final preparation will use technetium$^{99m}$ pertechnetate and hexamethylpropyleneamine oxime (Tc$^{99m}$-HMPAO) to label MSCs and will follow the position of the cells after using PAAG as a scaffold in the intratendinous injection in 3 normal horses. This final part of the protocol has not been completed.

In all tendinous or ligamentous structures the injection was difficult due to the hardness of the normal tissue. During the ultrasonographic monitorization gel started being visible as a hypoechoic image, mixed with air introduced by the needle. After injecting over 0.2-0.3 ml the gel started being visible outside the tendon core. In the structures with smaller section, as the SDFT or the LB no more than 0.2 ml could be retained in the core.

Even though no lameness was present after injection, and no severe swelling or infection was encountered, in all cases a small swelling over the injection site was visible after 3 h (FIG. 4a). It remained visible during the complete time that the limbs were examined, up to 21 days in some cases. Deep pain on the injection site was present during 2 to 5 days.

Figure 4:
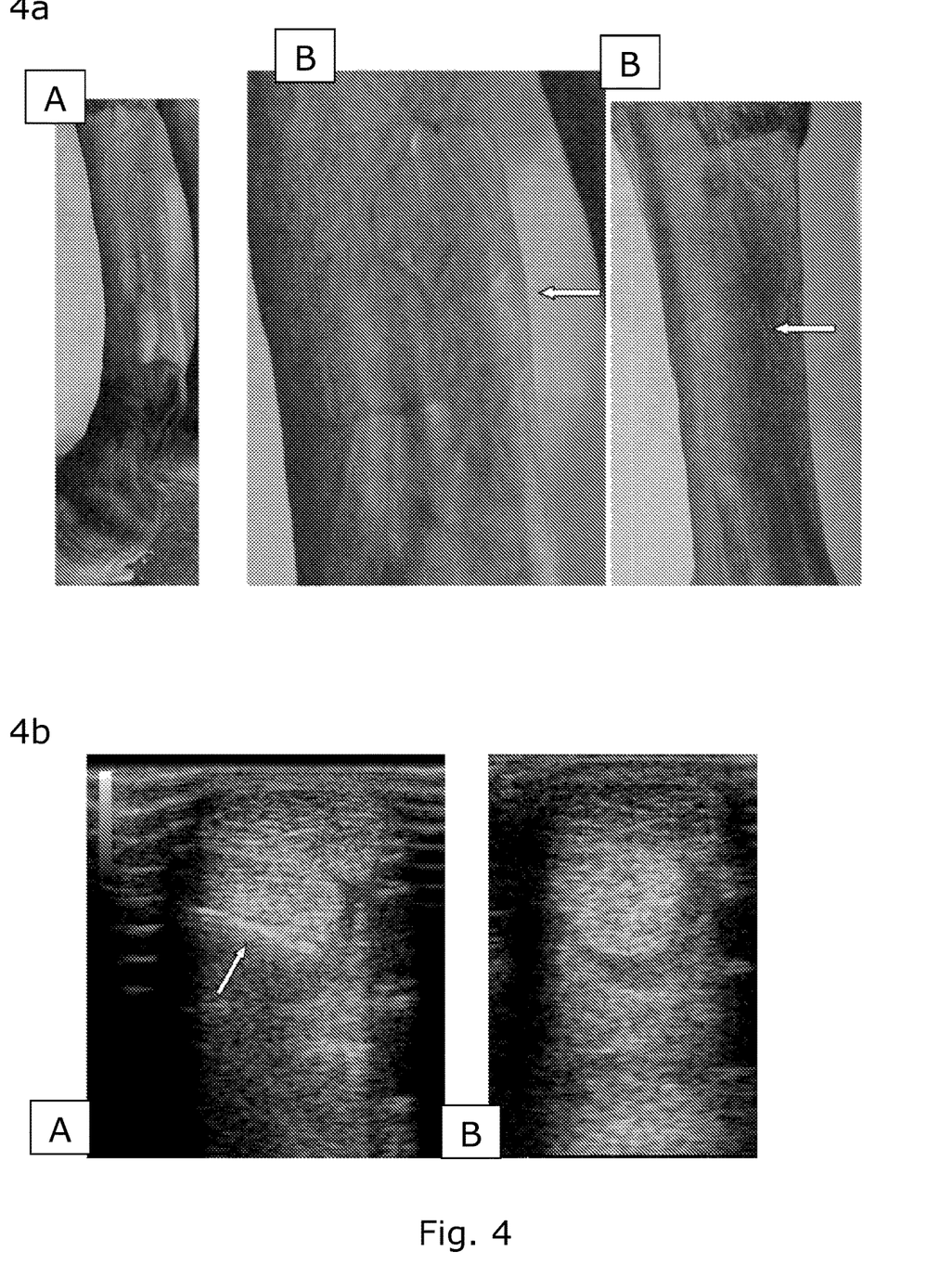

FIG. 4 shows 14 days post injection the external aspect of a limb where the deep digital flexor tendon was injected. A: view of the entire distal limb. B: detail over the injection site. The swelling (white arrows) was noticeable on both the palmar and lateral aspects.

Ultrasonographically the PAAG was not visible after 3 hours, neither inside the tendon nor in the soft tissue surrounding the tendon (FIG. 4b). FIG. 4b shows an ultrasonographic image of the case corresponding to FIG. 4a. The flexor tendinous structures of the mid metacarpal region. A: image corresponding immediately after the intratendinous injection. The air is visible after depositing the PAAG. B: the area of injection 24 h after injection. No hypoechoic PAAG can be imaged, despite the swelling present.

Conclusions on the Clinical Trial

The use of PAAG is safe when administered in normal equine tendons since no infection, adverse reaction or lameness was associated with the treatment in 18 cases. The assessment of the amount of gel that remained inside the tendon was not possible. During the injection the hypoechoic ultrasonographic appearance of the gel disappeared of the image, possibly at least partially, due to the pressure that the ultrasound probe had to exert over the injection site.

Only a small volume of gel can be retained in the tendon core. After 0.1 ml of gel the air and the gel start being imaged outside the tendon. It is not known if the pressure of the ultrasonographic probe may have decreased the volume of PAAG that a normal tendon may hold inside. The accepted protocol used in clinical cases for intralesional treatment in tendinopathy was mimicked.

It must be noted that a normal tendon provides a homogeneous and highly fibrous tissue, quite difficult to inject. Moreover, the PAAG has a high viscosity and thickness. However, it should be noted that tendinopathy lesions presents a lower resistance to injection.

The small swelling that remained in the injection area for as long as 3 weeks is a non-cosmetic result for most equine patients. The ultrasonographic exam did not reveal any hypoechoic image, and the swelling disappeared under the pressure of the ultrasound probe. It may be caused by the gel that stays in the peritendinous area and that is displaced transiently during ultrasonographic examination. The thickness under the skin could also be caused by inflammation and fibrous reaction caused by the PAAG.

Example 3.2—Distribution of MSCs After Implantation in the Joint of a Horse

Figure 5:
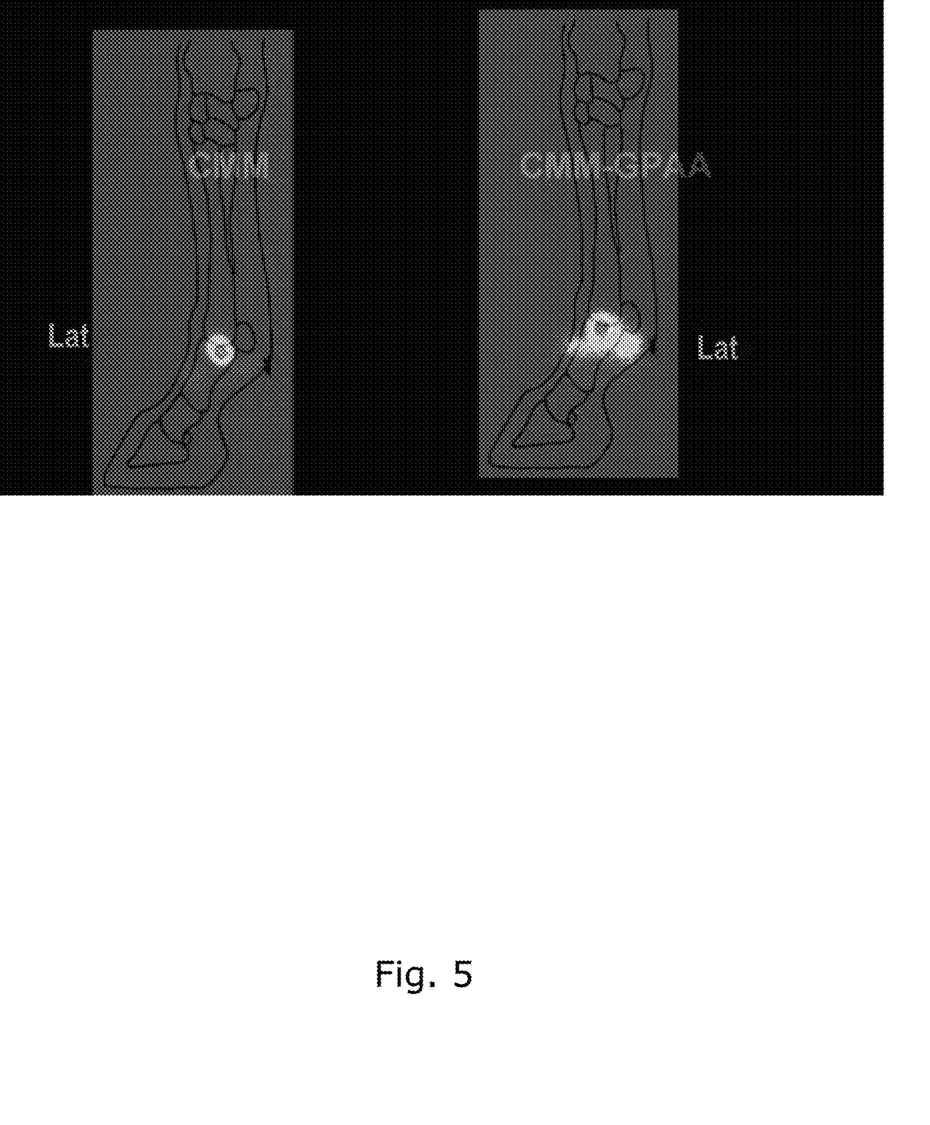
FIG. 5 shows the distribution of MSCs after implantation in the joint of a horse. The MSCs have been vehiculated in plasma (left figure) or in PAAG (right figure).

MSCs Vehiculated in Plasma and PAAG:

FIG. 5a shows a comparison of the distribution of MSCs vehiculated in plasma and PAAG in the joint of a horse.

Lateral projection of planar gammascintigraphy of a metacarpophalangeal joint 1 hour after implantation of MSCs labelled with Tc99-HMPAO. Cells were implanted vehiculated on plasma (CMM) (left side of figure) and in PAAG as a scaffold (CMM-GPAA) (right side of figure). MSCs remain concentrated at the injection site; however, the use of PAAG as a scaffold allows a more even distribution of the cells within the joint.

Summary of Results of Vitro Study and In Vivo Study—Examples 2 and 3

The in vitro study performed has demonstrated the use of PAAG as a scaffold for MSCs in the horse. The PAAG surprisingly preserves the viability and migration of the MSCs, and its engraftment into the tendon matrix occurs. Also surpringly, and important too, there is no inflammatory response modulated by IL-1β as this was undetectable in preliminary investigations.

Further, the use of PAAG is safe when administered in normal equine tendons since no infections, adverse reactions or lameness was associated with the treatment in 18 cases. Also, the use of PAAG as a scaffold for MSCs in the horse allows a more even distribution of the cells within the joint.

Example 3.3—Clinical Trial—MSCs After Implantation in the Joint of Horses with Tendon Injury According to the present invention, 3 cases of horses with bilateral naturally occurring tendinopathy (total joints treated n=6) will receive implantation of 10 millions allogenic MSCs in both joints. In one limb MSCs and contralateral MSCs-PAAG. The implant is Tc99 HMPAO labelled MSCs with and without PAAG. Nuclear scintigraphy will be performed at 0 h, 1 h, 3 h, 6 h, 12 h, 24 h and 36 h for comparison of distribution and retention on each treatment. The horses will be evaluated for the same changes in physical characteristics as discussed in Example 3.1—Safety of injection of PAAG demonstrated in a clinical trial. Further, the aim will be to evaluate whether lameness and/or limping is improved and if the treatment with MSCs with or without PAAG is physically tolerable for the joints of the horses. Follow up will be performed after 1 weeks, 2 weeks, 1 month, 3 months, 6 months, 24 months, 36 months and 48 months.

TABLE 5

Results of clinical trial of horses with bilateral tendinopathy

| | Duration | | | | | | | |
|---|---|---|---|---|---|---|---|---|
| | 1 week | 2 weeks | 1 month | 3 months | 6 months | 1 year | 1.5 years | 2 years |
| Physically tolerable | Yes | Yes | Yes | Yes | Yes | Yes | Yes | Yes |
| Improves joint (less limping/no lameness) | No | No | Yes | Yes | Yes | Yes | Yes | Yes |

When scoring the "Physically tolerable" parameter in Table 5, the veterinarian will detect the same parameters that were measured and presented in Example 3.1. This means that the veterinarian will monitor rectal temperature, contour of the limb, palpation of the injection area and presence of lameness at walk of the horses. Haematology and fibrinogen will be measured before the injection and at day 3 and 7 post injection. If all parameters are acceptable, a "yes" score is obtained. Improvement in joints (less limping/no lameness) will be evaluated by the veterinarian by visual inspection.

REFERENCES

Smith R K, Korda M, Blunn G W, Goodship A E. Isolation and implantation of autologous equine mesenchymal stem cells from bone marrow into the superficial digital flexor tendon as a potential novel treatment. Equine Vet J 2003;35:99-102.

Narins R. S. and Schmidt R., "Polyacrylamide Hydrogel Differences: Getting rid of the confusion", Journal of Drugs in Dermatology, Vol 10, Issue 12, December 2011, p. 1370.

The inevntion claimed is:

1. A composition comprising stem cells; a cell culture medium; and a polyacrylamide hydrogel,
    wherein the polyacrylamide hydrogel comprises acrylamide monomers, a cross-linking agent, and N-hydroxyethyl acrylamide (HEA), wherein a weight percent of the HEA is greater than 0% and less than 0.02% of a total weight of the polyacrylamide hydrogel,
    wherein an elasticity modulus of the polyacrylamide hydrogel is 1 to 200 Pa,
    wherein the stem cells are mesenchymal stem cells,
    wherein a molar ratio of the acrylamide monomers and the cross-linking agent is from 150:1 to 1000:1, and
    wherein the mesenchymal stem cells are encapsulated in the polyacrylamide hydrogel such that the polyacrylamide hydrogel supports viability and proliferation of the stem cells.

2. The composition according to claim 1, wherein the polyacrylamide hydrogel has the elasticity modulus of about 5 to 150 Pa.

3. The composition according to claim 1, wherein the polyacrylamide hydrogel has a dry matter content of about 0.5 to 25%.

4. The composition according to claim 1, wherein the cross-linking agent comprises N,N'-methylene-bis-acrylamide (bisAM).

5. The composition according to claim 4, wherein the molar ratio between the acrylamide monomers and the cross-linking agent is from 175:1 to 800:1.

6. The composition according to claim 1, wherein the molar ratio between the acrylamide monomers and the cross-linking agent is from 175:1 to 800:1.

7. A process for making the composition according to claim 1, comprising:
    i. providing stem cells, a cell culture medium and a polyacrylamide hydrogel, wherein the polyacrylamide hydrogel comprises acrylamide monomers, a cross-linking agent, and N-hydroxyethyl acrylamide (HEA), wherein a weight percent of the HEA is greater than 0% and less than 0.02% of a total weight of the polyacrylamide gel,
    wherein an elasticity modulus of the polyacrylamide hydrogel is 1 to 200 Pa,
    wherein a molar ratio of the acrylamide monomers and the cross-linking agent is from 150:1 to 1000:1,
    wherein the stem cells are mesenchymal stem cells; and
    ii. mixing the components of i) thereby achieving the composition,
    wherein the mesenchymal stem cells are encapsulated in the polyacrylamide hydrogel such that the polyacrylamide hydrogel supports viability and proliferation of the stem cells.

8. A method of making a pharmaceutical composition comprising incorporating the composition of claim 1 into a formulation suitable for human administration.

9. The method according to claim 8, wherein the formulation is an injectable formulation.

10. A method of improving a tendon injury in a mammal comprising providing the composition of claim 1 to a mammal in need thereof.

11. The method according to claim 10, wherein the mammal is selected from a human, a racing mammal or a companion mammal.

12. The method according to claim 10, wherein the tendon injury is selected from one or more of trauma, rupture, tearing or ulcerative inflammation.

13. The method according to claim 10, wherein the tendon injury is selected from one or more of tendinitis, tendinosis or tendinopathy.

14. The method according to claim 11, wherein the racing mammal is a horse or the mammal to be treated is a human or the companion mammal to be treated is a dog.

15. The method according to claim 11, wherein the composition is administered by injection.

* * * * *

UNITED STATES PATENT AND TRADEMARK OFFICE
CERTIFICATE OF CORRECTION

PATENT NO. : 11,969,523 B2
APPLICATION NO. : 16/607304
DATED : April 30, 2024
INVENTOR(S) : Ankorina-Stark et al.

Page 1 of 3

It is certified that error appears in the above-identified patent and that said Letters Patent is hereby corrected as shown below:

On the Title Page

Item (57), Line 4, delete "$W_{monomer}/W_{total\ PAAC}]$" and insert -- $W_{monomer}/W_{total\ PAAC}$ --.

In the Specification

Column 2, Line 17 (approx.), delete "dimentional" and insert -- dimensional --.

Column 2, Line 29 (approx.), delete ""Notrex," insert -- Noltrex™ --.

Column 3, Line 11-12, delete "$W_{monomer}/W_{total\ PAAC}]$" and insert -- $W_{monomer}/W_{total\ PAAC}$ --.

Column 3, Line 40, delete "$W_{monomer}/W_{total\ PAAC}]$" and insert -- $W_{monomer}/W_{total\ PAAC}$ --.

Column 3, Line 50, delete "$W_{monomer}/W_{total\ PAAC}]$" and insert -- $W_{monomer}/W_{total\ PAAC}$ --.

Column 3, Line 60, delete "$W_{monomer}/W_{total\ PAAC}]$" and insert -- $W_{monomer}/W_{total\ PAAC}$ --.

Column 5, Line 19, delete "MSCS" and insert -- MSCs --.

Column 5, Line 20, delete "days" and insert -- days. --.

Column 5, Line 47, delete "4a." and insert -- FIG. 4a. --.

Column 6, Line 61, delete "$W_{monomer}/W_{total\ PAAC}]$" and insert -- $W_{monomer}/W_{total\ PAAC}$ --.

Column 6, Line 66, delete "$W_{monomer}/W_{total\ PAAC}]$" and insert -- $W_{monomer}/W_{total\ PAAC}$ --.

Column 7, Line 4, delete "$W_{monomer}/W_{total\ PAAC}]$" and insert -- $W_{monomer}/W_{total\ PAAC}$ --.

Signed and Sealed this
Twelfth Day of November, 2024

*Katherine Kelly Vidal*

Katherine Kelly Vidal
*Director of the United States Patent and Trademark Office*

Column 7, Line 30-31 (approx.), delete "$W_{monomer}/W_{total\ PAAC}]$" and insert -- $W_{monomer}/W_{total\ PAAC}$ --.

Column 7, Line 41-42 (approx.), delete "$W_{monomer}/W_{total\ PAAC}]$" and insert -- $W_{monomer}/W_{total\ PAAC}$ --.

Column 7, Line 61-65 (approx.), delete " 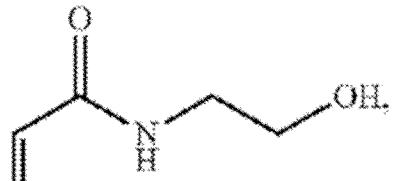 " and insert --.

Column 8, Line 43, delete "$W_{monomer}/W_{total\ PAAC}]$" and insert -- $W_{monomer}/W_{total\ PAAC}$ --.

Column 8, Line 57, delete "The a" and insert -- The --.

Column 8, Line 60, delete "McCoys 5A Hams F-12." and insert -- McCoy's 5A, Ham's F-12. --.

Column 10, Line 20, delete "$W_{monomer}/W_{total\ PAAC}]$" and insert -- $W_{monomer}/W_{total\ PAAC}$ --.

Column 10, Line 27, delete "$W_{monomer}/W_{total\ PAAC}]$" and insert -- $W_{monomer}/W_{total\ PAAC}$ --.

Column 10, Line 34, delete "$W_{monomer}/W_{total\ PAAC}]$" and insert -- $W_{monomer}/W_{total\ PAAC}$ --.

Column 11, Line 33, delete "tendinosus," and insert -- tendinosis, --.

Column 12, Line 57, delete "actiivity" and insert -- activity --.

Column 15, Line 63, Before "300:1," delete "about".

Column 16, Line 26, delete "PAGG" and insert -- PAAG --.

Column 17, Line 18, delete "tetracetic" and insert -- tetraacetic --.

Column 17, Line 19, delete "tetracetic" and insert -- tetraacetic --.

Column 18, Line 7 (approx.), delete "syringe" and insert -- syringe. --.

Column 19, Line 13 (approx.), delete "1v11 1v11 1v12" and insert -- 1v11 1v12 1v13 --.

Column 19-20, Line 47 (approx.), delete "fpre-wash" and insert -- f pre-wash --.

CERTIFICATE OF CORRECTION (continued)
U.S. Pat. No. 11,969,523 B2

Column 22, Line 9, delete "Encapsulated in PAAG is the Outcome" and insert -- encapsulated in PAAG is the outcome. --.

Column 22, Line 58, delete "heatocytometer." and insert -- hemocytometer. --.

Column 22, Line 59, delete "celle" and insert -- cell --.

Column 23, Line 56, delete "flourescent" and insert -- fluorescent --.

Column 24, Line 45 (approx.), delete "metacarpofalangeal" and insert -- metacarpophalangeal --.

Column 26, Line 20, delete "gammascintigraphy" and insert -- gamma scintigraphy --.

Column 26, Line 36 (approx.), delete "surpringly," and insert -- surprisingly, --.